United States Patent
Bradbury et al.

(10) Patent No.: US 11,947,344 B2
(45) Date of Patent: Apr. 2, 2024

(54) METHOD OF OPERATING A DIAGNOSTIC INSTRUMENT

(71) Applicant: Roche Diagnostics Operations, Inc., Indianapolis, IN (US)

(72) Inventors: Christopher Bradbury, Zurich (CH); Scott Perala, Urdorf (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 539 days.

(21) Appl. No.: 16/807,777

(22) Filed: Mar. 3, 2020

(65) Prior Publication Data
US 2020/0310395 A1 Oct. 1, 2020

(51) Int. Cl.
*G05B 19/418* (2006.01)
*G01N 35/00* (2006.01)

(52) U.S. Cl.
CPC ... *G05B 19/41865* (2013.01); *G01N 35/0092* (2013.01); *G05B 2219/32283* (2013.01); *G05B 2219/32356* (2013.01)

(58) Field of Classification Search
CPC .... G05B 19/41865; G05B 2219/32283; G05B 2219/32356; G16H 40/40; G01N 35/0092
See application file for complete search history.

(56) References Cited

U.S. PATENT DOCUMENTS

| | | | |
|---|---|---|---|
| 8,597,569 B2* | 12/2013 | Gruen | A61L 2/10 345/173 |
| 9,323,894 B2 | 4/2016 | Kiani | |
| 10,732,603 B2* | 8/2020 | Chao | G16C 20/90 |
| 11,080,848 B2* | 8/2021 | Dimov | G16H 10/40 |
| 11,112,399 B2* | 9/2021 | Karup | G01N 35/00732 |
| 11,230,690 B2* | 1/2022 | Cannon | H04W 4/38 |
| 2006/0188389 A1* | 8/2006 | Levy | A61L 2/10 422/186.3 |
| 2007/0195550 A1* | 8/2007 | Tsai | F21V 33/0052 362/600 |
| 2007/0196235 A1* | 8/2007 | Shur | C02F 1/325 422/62 |
| 2007/0205382 A1* | 9/2007 | Gaska | A61L 2/10 250/492.1 |

(Continued)

FOREIGN PATENT DOCUMENTS

| | | |
|---|---|---|
| JP | H08-340527 A | 12/1996 |
| JP | 2002-162400 A | 6/2002 |

(Continued)

OTHER PUBLICATIONS

European Search Report dated Sep. 9, 2019, in Application No. EP 19164964.4, 2 pp.

*Primary Examiner* — Shogo Sasaki
(74) *Attorney, Agent, or Firm* — Roche Diagnostics Operations, Inc.

(57) ABSTRACT

A computer implemented method of operating a diagnostic instrument such that maintenance processes do not conflict with operator activity is presented. A maintenance process conflicts with operator activity if the probability of use of the diagnostic instrument is above a usage probability threshold. The probability of use of the diagnostic instrument is determined based on detected presence and/or movement of an operator in the proximity of the diagnostic instrument and/or operation of the diagnostic instrument.

15 Claims, 7 Drawing Sheets

(56) References Cited

U.S. PATENT DOCUMENTS

| | | | | |
|---|---|---|---|---|
| 2007/0258852 A1* | 11/2007 | Hootsmans | ............... | A61L 2/10 |
| | | | | 422/186 |
| 2008/0067417 A1* | 3/2008 | Lane | ........................ | A61L 2/24 |
| | | | | 250/455.11 |
| 2011/0117968 A1* | 5/2011 | Eromaki | ............. | G06F 3/04886 |
| | | | | 345/173 |
| 2011/0256019 A1* | 10/2011 | Gruen | ........................ | A61L 2/10 |
| | | | | 345/173 |
| 2012/0108931 A1 | 5/2012 | Taub et al. | | |
| 2013/0045685 A1* | 2/2013 | Kiani | .................... | G08B 21/24 |
| | | | | 340/5.6 |
| 2016/0015329 A1 | 1/2016 | Kohlrausch et al. | | |
| 2017/0300641 A1 | 10/2017 | Qerim et al. | | |

FOREIGN PATENT DOCUMENTS

| | | |
|---|---|---|
| JP | 2014-163855 A | 9/2014 |
| WO | 2015/069503 A2 | 5/2015 |
| WO | 2017/002477 A1 | 1/2017 |

\* cited by examiner

Operation after presence
e.g. finishing tests

METHOD OF OPERATING A DIAGNOSTIC INSTRUMENT

CROSS-REFERENCE TO RELATED APPLICATIONS

This application is a continuation of EP 19164964.9, filed Mar. 25, 2019, which is hereby incorporated by reference.

BACKGROUND

The present disclosure generally relates to a computer-implemented method of operating a diagnostic instrument such as, an in-vitro diagnostic instrument.

In vitro diagnostic testing can have a major effect on clinical decisions, providing physicians with pivotal information. Diagnostic instruments such as, for example, in-vitro diagnostic instruments, perform a multitude of analyses on biological samples in order to determine physiological and biochemical states of patients, which can be indicative of a disease, nutrition habits, drug effectiveness, organ function and the like.

One field of diagnostic testing is conducted with routine analytical instruments in laboratories. These instruments are operated by operators that are educated to maintain and operate such instruments.

Another field of diagnostic testing is point of care (POC) testing or bedside testing. This type of diagnostic testing is performed mainly by nurses or medical staff primarily trained to operate the instruments available at the site of patient care, such as hospitals, emergency departments, intensive care units, primary care settings, medical centers, patient homes, a physician's office, a pharmacy or a site of an emergency.

Often, POC testing needs to meet clinical and laboratory requirements for short turnaround times (TAT) in critical care. Rapid determination of time-critical parameters (e.g. blood glucose, cardiac markers, blood gases, and the like) can accelerate decision making in the emergency room, intensive care units or even in the primary care setting. Point of care testing has become established worldwide and finds vital roles in public health. Potential operational benefits of point of care testing include: faster decision making, reduced operating times, postoperative care time, reduced emergency room time, reduced number of outpatient clinic visits, reduced number of hospital beds required, more optimal use of professional time.

Major benefits are obtained when the output of a POC diagnostic instrument is made available immediately. Results can be shared instantaneously with all members of the medical team enhancing communication by decreasing turnaround time (TAT).

However, it has been observed that often the availability of POC diagnostic instruments is impaired by maintenance and routine activities, such as quality control, calibration, system updates. During such activities, the diagnostic instruments are not available for diagnostic testing of patient biological samples, leading to increased turnaround times/delayed results. While efforts have been made to reduce the frequency and/or duration of such maintenance activities, these still have a considerable impact on the availability/readiness of the POC diagnostic instruments.

Hence, there is a need for a method of operating a point of care diagnostic instrument such as, for example, a diagnostic instrument and a computer program product for a diagnostic instrument, which improves the availability/readiness of the point of care diagnostic instruments for diagnostic testing of patient's biological samples.

SUMMARY

According to the present disclosure, a method of operating a diagnostic instrument for analyzing a biological sample comprising an analytical unit configured to carry out one or more analytical processing steps on the biological sample to determine presence, absence and/or concentration of one or more analyte(s) in the biological sample is presented. The method can comprise detecting activity in the proximity of the diagnostic instrument by a detection unit. Activity can comprise presence and/or movement of an operator in the proximity of the diagnostic instrument and/or operation of the diagnostic instrument by an operator. The method can also comprise processing signals of the detection unit by a processor to determine a probability of use of the diagnostic instrument. The probability of use can be directly proportional to the activity in the proximity of the diagnostic instrument. The method can also comprise carrying out maintenance processes by the diagnostic instrument such as not to conflict with the activity. A maintenance process can conflict with the activity if the probability of use of the diagnostic instrument is above a usage probability threshold.

Accordingly, it is a feature of the embodiments of the present disclosure to provide for a method of operating a point of care diagnostic instrument, which improves the availability/readiness of the point of care diagnostic instruments for diagnostic testing of patient's biological samples. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
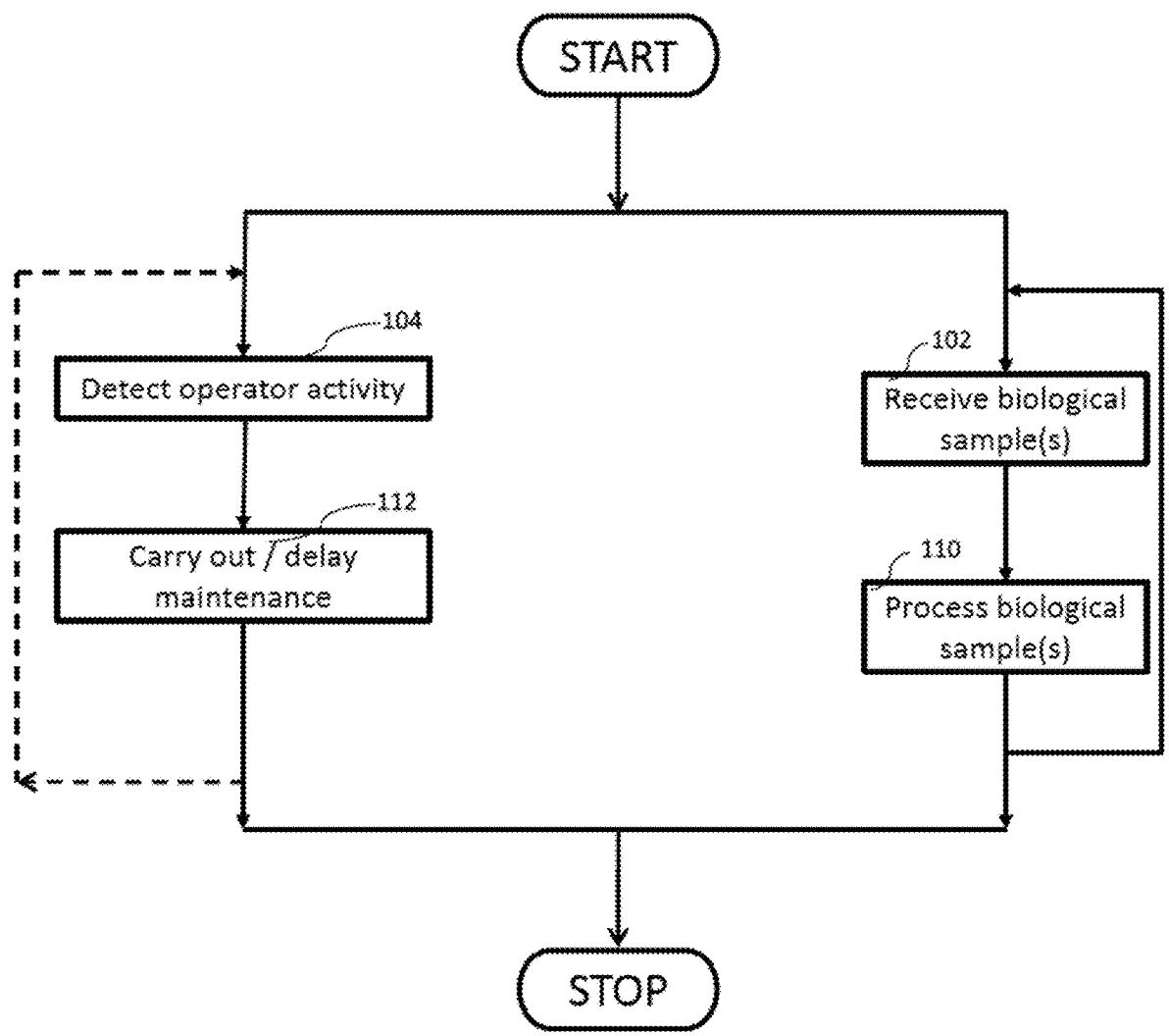
FIG. 1 illustrates a method flowchart according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

Embodiments herein disclosed derive from the observation that—despite maintenance activities statistically occupying diagnostic instruments for a relatively small amount of time-users reported such tasks having a significant impact on their activities. It has been identified that, in addition to the frequency and duration of the maintenance activities, the timing of maintenance activities has a great impact on the perceived availability/readiness of the point of care (POC) diagnostic instruments. For example, if maintenance activities are performed while users are actively using or about to actively use the diagnostic instrument, then even if the maintenance activity is of short duration, the user perceives this maintenance activity as greatly impacting his/her work. On the other hand, maintenance activities performed at times when the diagnostic instrument is unlikely to be used (e.g. lunch break, night shift) have a lower perceived impact on instrument availability, despite the fact that objectively they take the same amount of time. Embodiments herein disclosed address the need to increase the perceived availability of diagnostics instruments by aiming to schedule maintenance activities of diagnostics instruments at times when the diagnostic instruments are not in use or least likely to be used. Therefore, even though the time required by the maintenance activities is not affected, the degree to which the maintenance activities affects users is reduced and, hence, the perceived availability of the diagnostics instruments is increased/improved.

Embodiments of the disclosed method address the above-identified need by detecting activity in the proximity of the diagnostic instrument by a detection unit, wherein activity can comprise presence and/or movement in the proximity of the diagnostic instrument and/or operation of the diagnostic instrument by an operator. Signals of the detection unit can then be processed by a processor to determine a probability of use of the diagnostic instrument. The probability of use can be directly proportional to the activity in the proximity of the diagnostic instrument. The diagnostic instrument can then carry out maintenance processes such as not to conflict with the activity, wherein a maintenance process conflicts with the activity if the probability of use of the diagnostic instrument is above a usage probability threshold. Carrying out maintenance processes such as not to conflict with the activity can comprise the diagnostic instrument interrupting and/or postponing maintenance processes if the probability of use of the diagnostic instrument is above a usage probability threshold.

According to further embodiments disclosed herein, the processor can determine an activity pattern based on signals of the detection unit. The activity pattern can be indicative of a probability of use at a specific time(s) and/or in a specific time interval. The probability of use at a specific time(s) and/or in a specific time interval can be proportional to the detected activity in the same time/time interval in the past, for example, in the same hour, weekday respectively between the same hours of a day, between the same days of a week. In order to ensure that maintenance processes of longer duration—which are scheduled in advance—also do not reduce the perceived availability of the instruments, the diagnostic instrument can then schedule maintenance processes of a second type with an expected duration longer than a threshold duration such as not to conflict with the activity pattern, wherein a maintenance processes conflicts with the activity pattern if the probability of use of the diagnostic instrument at the time the maintenance process is scheduled to be carried out is above a usage probability threshold. Hence, when the diagnostic instrument executes the maintenance processes at the scheduled time/time interval, the probability that the instrument needs to be used can be below the set threshold.

According to further embodiments disclosed herein, a network of a plurality of diagnostic instruments can be communicatively connected to detect activity in the proximity of a plurality of diagnostic instruments. To avoid that all instruments are executing maintenance processes and to ensure that at least one instrument is available for analyzing patient sample(s), maintenance processes of the plurality of diagnostic instruments can be scheduled at different times/time intervals such as to avoid that all diagnostic instruments are executing a maintenance process at the same time.

The terms 'sample', 'patient sample' and 'biological sample' can refer to material(s) that may potentially contain an analyte of interest. The patient sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The patient sample can be pretreated prior to use, such as preparing plasma from blood, diluting viscous fluids, lysis or the like. Methods of treatment can involve filtration, distillation, concentration, inactivation of interfering components, and the addition of reagents. A patient sample may be used directly as obtained from the source or used following a pretreatment to modify the character of the sample. In some embodiments, an initially solid or semi-solid biological material can be rendered liquid by dissolving or suspending it with a suitable liquid medium. In some embodiments, the sample can be suspected to contain a certain antigen or nucleic acid.

The term 'analyte' can be a component of a sample to be analyzed, e.g., molecules of various sizes, ions, proteins, metabolites and the like. Information gathered on an analyte may be used to evaluate the impact of the administration of drugs on the organism or on particular tissues or to make a diagnosis. Thus, 'analyte' can be a general term for substances for which information about presence, absence and/or concentration is intended. Examples of analytes can be, for example, glucose, coagulation parameters, endogenic proteins (e.g., proteins released from the heart muscle), metabolites, nucleic acids, ions, gases and so on.

The term 'analysis' or 'analytical test' as used herein can encompass a laboratory procedure characterizing a parameter of a biological sample for qualitatively assessing or quantitatively measuring the presence or amount or the functional activity of an analyte.

The term 'reagent' as used herein can refer to materials necessary for performing an analysis of analytes, including reagents for sample preparation, control reagents, reagents for reacting with the analyte to obtain a detectable signal, and/or reagents necessary for detecting the analyte. Such reagents may include reagents for isolating an analyte and/or reagents for processing a sample and/or reagents for reacting with an analyte to obtain a detectable signal and/or washing reagents and/or diluents.

The term 'reagent cassette' as used herein can refer to any vessel/container comprising a liquid or suspension of reagents. Alternatively, a reagent cassette can be a holder for holding container(s) comprising a liquid or a suspension of reagents.

The term 'Quality control' or 'analytical quality control' can refer to all those processes and procedures designed to ensure that the results of laboratory analysis (analytical tests) are consistent, comparable, accurate and within specified limits of precision.

The term 'quality control (QC)' materials as used herein can refer to any composition with known concentration of an analyte, such as positive and negative controls, that can serve the purpose of providing evidence that an analytical test is successfully performed and is giving the expected level of sensitivity and specificity as characterized during technical optimization and validation of the analytical test for diagnostic use. In other words, a 'quality control' can be used as referring to a physical sample used in one or several monitoring processes to monitor the performance of particular tests or assays of an analyzer. Positive controls primarily monitor calibration of the system and sensitivity. Negative controls are primarily used to evaluate the specificity of the analytical tests to identify false-positive results.

The term 'diagnostic instrument'/'analytical instrument' as used herein can encompass any apparatus or apparatus component configured to determine presence, absence and/or concentration of one or more analyte(s) in the biological sample by carrying out one or more analytical processing steps on the biological sample. A diagnostic instrument can be operable to determine via various chemical, biological, physical, optical or other technical procedures a parameter value of the sample or a component thereof. A diagnostic instrument may be operable to measure the parameter of the sample or of at least one analyte and return the obtained measurement value. The list of possible analysis results returned by the analyzer can comprise, without limitation, concentrations of the analyte in the sample, a digital (yes or no) result indicating the existence of the analyte in the sample (corresponding to a concentration above the detection level), optical parameters, DNA or RNA sequences, data obtained from mass spectrometry of proteins or metabolites and physical or chemical parameters of various types. A diagnostic instrument may comprise units assisting with the pipetting, dosing, and mixing of samples and/or reagents. The diagnostic instrument may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The diagnostic instrument may comprise a process and detection system whose workflow is optimized for certain types of analysis. Examples of such diagnostic instrument can be clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

The term 'maintenance process' as used herein can refer to any activity required to be performed on a diagnostic instrument in order to keep the instrument operational and within expected parameters, satisfying regulatory, compliance and quality specifications. A maintenance process can comprise but may not be limited to quality control procedures, calibration processes, instrument updates (SW), loading of consumables such as reagents, quality control or calibrator material, and the like.

The term 'processor' as used herein can encompass any physical or virtual processing device configurable to control a laboratory instrument or system comprising one or more laboratory instruments in a way that workflow(s) and workflow step(s) are conducted by the laboratory instrument/system. The control unit may, for example, instruct the laboratory instrument/system to conduct pre-analytical, post analytical and analytical workflow(s)/workflow step(s) as well as to carry out maintenance processes. The processor may receive information from a data management unit regarding which steps need to be performed with a certain sample.

The term 'communication network' as used herein can encompass any type of wireless network, such as a WiFi™, GSM™, UMTS or other wireless digital network or a cable based network, such as Ethernet™ or the like. In particular, the communication network can implement the Internet protocol (IP). For example, the communication network can comprise a combination of cable-based and wireless networks.

The term 'user interface' as used herein can encompass any suitable piece of software and/or hardware for interactions between an operator and a machine, including but not limited to a graphical user interface (GUI) for receiving as input a command from an operator and also to provide feedback and convey information thereto. Also, a system/device may expose several user interfaces to serve different kinds of users/operators.

A method for operating a diagnostic instrument for analyzing a biological sample is disclosed. The diagnostic instrument can comprise an analytical unit, which can be configured to carry out one or more analytical processing steps on the biological sample to determine presence, absence and/or concentration of one or more analyte(s) in the biological sample.

FIG. 1 illustrates a first embodiment of the disclosed method, wherein the instrument carries out maintenance activities such as not to conflict with currently detected activity around the instrument. As shown on FIG. 1, the receipt and processing of biological samples such as the maintenance activities can be (as a whole) parallel activities. Start and stop on the flowcharts can be, for example, the start-up or shutdown of the instrument. Since the step 102 of receipt of biological samples and the processing of biological samples in step 110 can be particular to the respective instruments are known, these steps shall not be described in greater detail as the inventive concepts disclosed herein are applicable to any type of diagnostic instrument.

In a step 104, human activity can be detected in the proximity of the diagnostic instrument by a detection unit. Activity can comprise the presence and/or movement of a person in the proximity of the diagnostic instrument and/or operation of the diagnostic instrument by an operator. Proximity in this context can be be understood to comprise anywhere from a few centimeters up to several meters such as, for example, the presence or movement in the same room as the instrument. Thereafter, signals of the detection unit can be processed by a processor of the instrument to determine a probability of use of the diagnostic instrument. The probability of use can be calculated as directly proportional to the activity in the proximity of the diagnostic instrument. For example, the probability of use can be calculated as a percentage proportional to the level of activity detected. For example, movement detected in five out of the last 10 minutes translates to a probability of use of 50% for a time interval of one minute. For maintenance processes of longer durations, longer time intervals can be considered, for example, if movement is detected five times in an hour, then the probability of use of an instrument can be considered "HIGH"; if it is three times, then "MEDIUM", while if one movement is detected then the probability of use of an instrument can be considered "LOW".

In subsequent step(s) 112, the diagnostic instrument can carry out/execute maintenance processes if the probability of use of the diagnostic instrument is below a usage probability threshold such as not to conflict with the activity. In other words, a maintenance process can conflict with the activity if the probability of use of the diagnostic instrument is above a usage probability threshold. Following up on the examples above, the maintenance process can be started/continued by the instrument if the probability of use (based on detected activity) is below 20%, or below "MEDIUM".

On one hand, avoiding conflict with detected activity can comprise the diagnostic instrument interrupting running maintenance processes if the probability of use of the diagnostic instrument is above a usage probability threshold. Whether the instrument can interrupt a maintenance activity can depend on the nature and progress of the respective maintenance activity. Usually interruptions are not possible in later phases to ensure the instrument can remain operational.

On the other hand, avoiding conflict with detected activity can comprise the diagnostic instrument postponing maintenance processes if the probability of use of the diagnostic instrument is above a usage probability threshold. Postponement can only be performed if correct operation of the instrument can be ensured, for example, if a calibration is still valid. The duration of the postponement can be dependent on the expected duration of the maintenance and the urgency of such.

Figure 2:
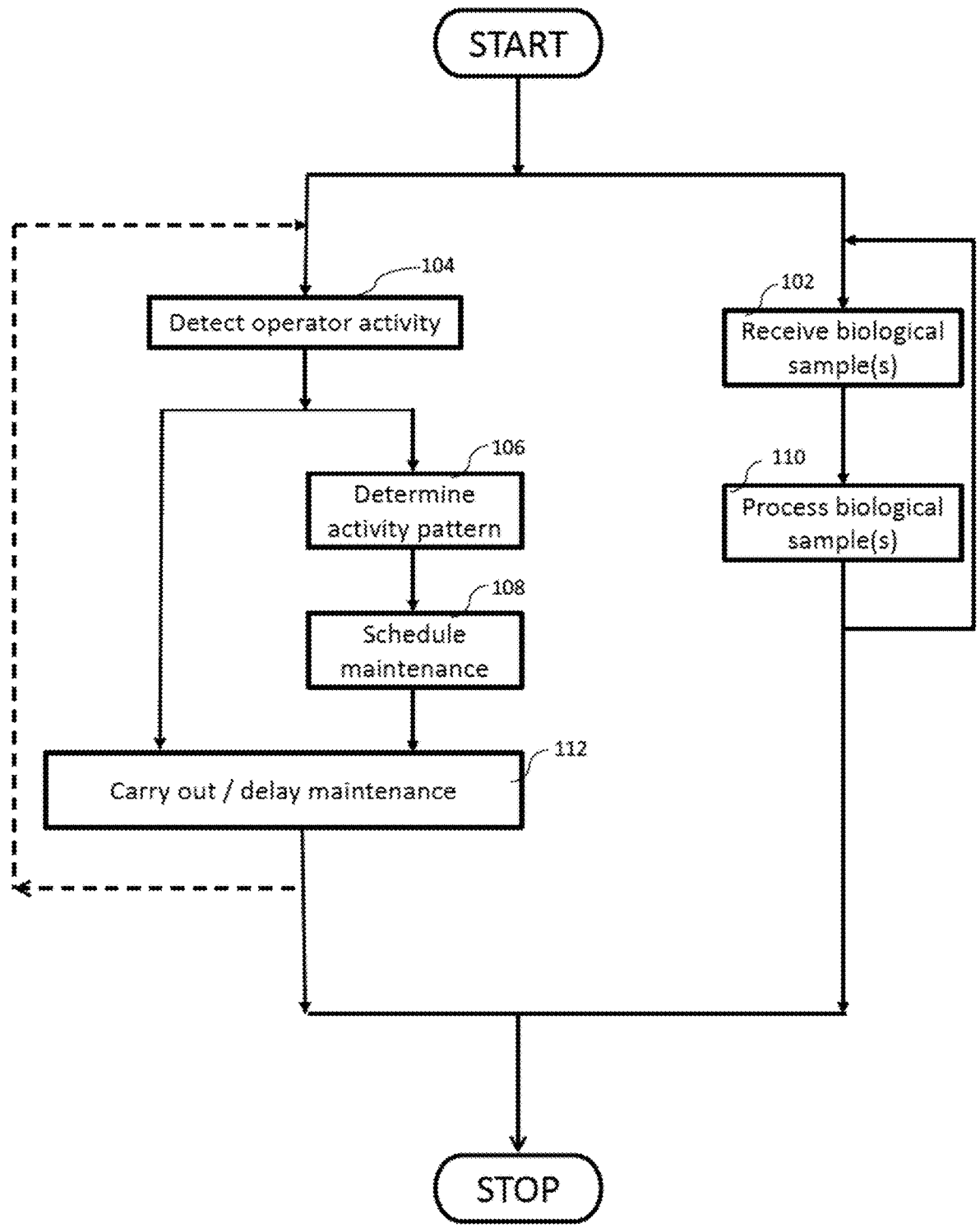
FIG. 2 illustrates a method flowchart according to another embodiment of the present disclosure.

Turning now to FIG. 2, a further embodiment of the disclosed method shall be described which can combine execution of maintenance processes so as not to conflict with detected activity and scheduling maintenance processes (of a second type—longer duration) so as not to conflict with a determined activity pattern.

As illustrated on FIG. 2, in a step 106, the processor can determine an activity pattern based on signals of the detection unit. The activity pattern can be indicative of a probability of use of the instrument not at the moment, but at a specific time(s) and/or in a specific time interval.

According to some embodiments, the determination of the activity pattern can be an iterative/learning process, the activity pattern becoming more and more precise with each activity detected. According to the various use cases, the activity pattern can be indicative of a probability of use of the instrument at a certain minute of each hour, a certain hour of a day, a certain day of the week, and the like.

In step 108, the diagnostic instrument can schedule maintenance processes of a second type with an expected duration longer than a threshold duration such as not to conflict with the activity pattern, wherein a maintenance process can conflict with the activity pattern if the probability of use of the diagnostic instrument at the time the maintenance process is scheduled to be carried out is above a usage probability threshold.

In step 122, the diagnostic instrument can execute the maintenance processes as scheduled.

Such embodiments can be particularly advantageous since they can allow optimal execution of both quicker maintenance activities as well as longer ones, which can be scheduled in advance.

Furthermore, according to some embodiments, determining an activity pattern can comprise one or more of the following: detecting activity using the detection unit at predetermined time intervals, calculating the probability of use in a specific time interval as an average or mean percentage of detected activity in each time interval, and/or identifying time intervals when probability of use in the proximity of the diagnostic instrument is above an intensive use threshold and pre-schedule maintenance processes of the diagnostic instrument at a time preceding time intervals above the intensive use threshold.

Intensive use can comprise, for example, emergency rooms or operating rooms, where it can be important that maintenance activities do not delay analytical testing, even if it means that certain maintenance activities are scheduled before the maximum interval expires.

According to further embodiments, the probability of use of the activity pattern can be increased for specific time(s) and/or time interval(s) in which instrument operation was detected immediately after completion of a maintenance process of the diagnostic instrument, since instrument operation immediately after completion of a maintenance process can be indicative that someone probably had to wait for the completion of a maintenance process.

In order to learn from and adapt to the particulars of a specific healthcare environment, according to further embodiments, determining an activity pattern can comprise one or more of the following: retrieving (from a database) an operator work schedule, wherein the work schedule can be indicative of time intervals in which an operator is on, respectively off-duty, and, furthermore, the work schedule may also comprise planned surgeries, time intervals when no maintenance process should prevent usage of an instrument; determining a correlation between the operator work schedule and detected activity, such as, for example, the probability of use of an instrument being lower if a high percentage of operators is off-duty; and extrapolate activity to entire work schedule based on the correlations. Such can be advantageous in the case of complete data regarding work schedules.

Since maintenance processes can be of different durations and keep an instrument unavailable for different times, according to some embodiments, the method can further comprise distinguishing between maintenance processes of a first type of maintenance processes having a first expected duration and a second type of maintenance processes having a second expected duration, the second duration being longer than the first duration. A maintenance process of a first type can conflict with the activity pattern if the probability of use of the diagnostic instrument, at the time the maintenance process of the first type is scheduled to be carried out, is above a first usage probability threshold and a maintenance process of a second type can conflict with the activity pattern if the probability of use of the diagnostic instrument, at the time the maintenance process of the second type is scheduled to be carried out, is above a second usage probability threshold, the second usage probability threshold being lower than the first usage probability threshold.

Illustrative Example

In a particular laboratory, the following maintenance activities need to be regularly performed:
1 point instrument calibration
  Duration: 3 minutes
  Frequency: every hour
2-point instrument calibration
  Duration: 7 minutes
  Frequency: every 12 hours
System calibration
  Duration: 15 minutes
  Frequency: every 24 hours
  For such an instrument, embodiments disclosed herein:
  Interrupt and/or postpone 1 point calibrations if probability of use of the diagnostic instrument based on current detected activity is above a usage probability threshold and if the last 1-point calibration was less than 1 hour ago;
  Schedule 2 point calibrations at a time in the 12-hour period such as not to conflict with the "typical" activity based on the activity pattern at the time interval of 1 hour before the expiry of 12 hours since the last 2-point calibration; and
  Schedule system calibrations at a time in the 24-hour period such as not to conflict with the "typical" activity based on the activity pattern in the time interval of 2 hours before the expiry of 24 hours since the last system calibration.

According to further embodiments, the processor can classify activity around the instrument into: a first group of activity if activity comprises operation (actual use) of the diagnostic instrument and a second group of activity if the detected activity comprises presence and/or movement in the proximity of the diagnostic instrument but not operation of the diagnostic instrument.

The probability of use of the diagnostic instrument corresponding to activity of the first group can be set higher than the probability of use of the diagnostic instrument corresponding to activity of the second group.

Figure 3:
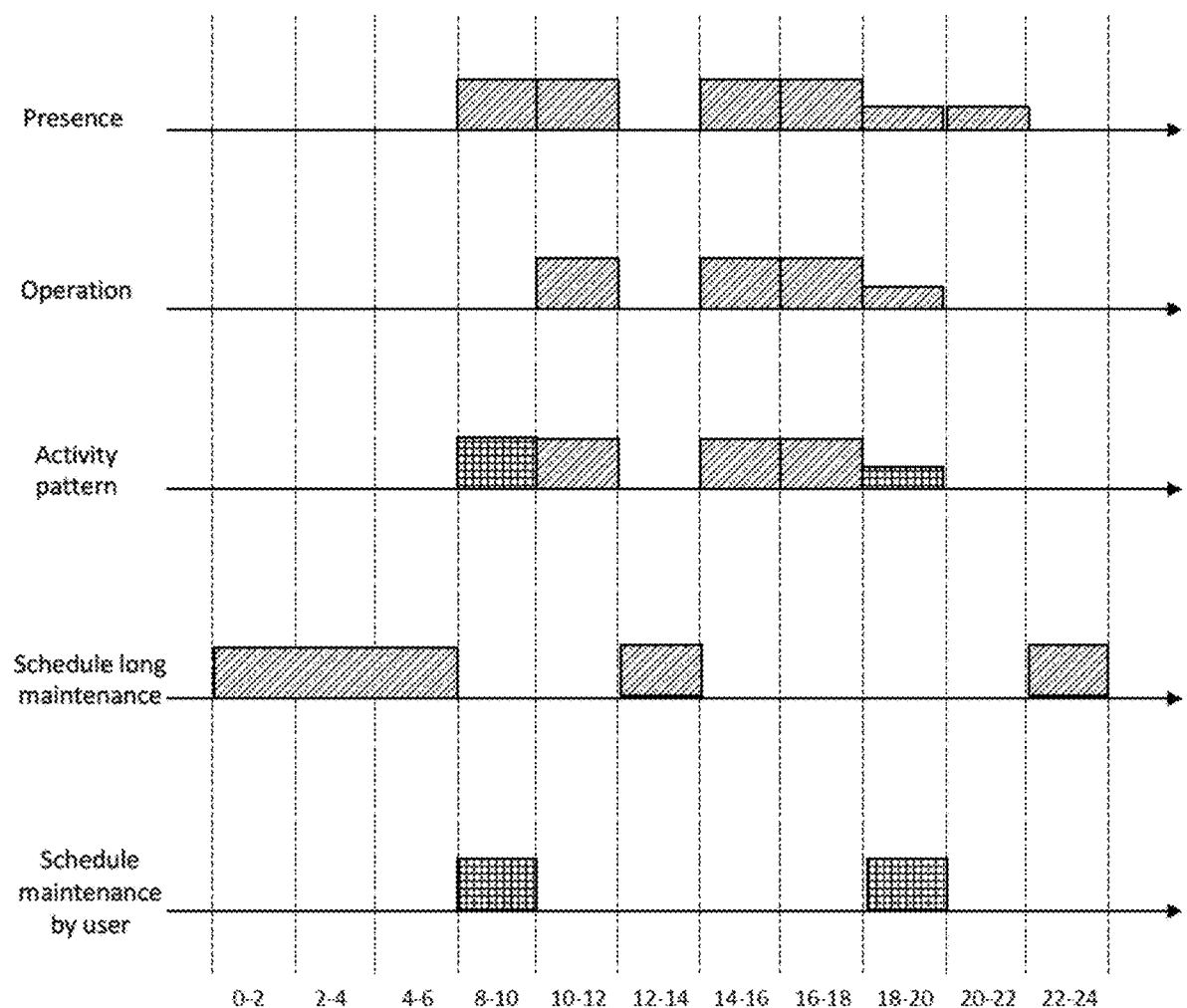
FIG. 3 illustrates a timeline illustrating detection of activity, determination of the activity pattern as well as scheduling of long duration activities and scheduling of activities requiring operator interaction according to an embodiment of the present disclosure.

FIG. 3 illustrates an example of determination of the activity pattern as well as scheduling of long duration activities and scheduling of activities requiring operator interaction. As illustrated on FIG. 3, further embodiments can further comprise scheduling maintenance processes requiring operator interaction at a specific time(s) and/or in a specific time interval with a probability of the second group of activity above an operator presence probability threshold.

Furthermore, according to even further embodiments, the processor can further distinguish between movement towards versus movement away from the instrument, the probability of use being higher in the first case.

Specific examples of different use cases shall now be described with reference to FIGS. 4-6.

Figure 4:
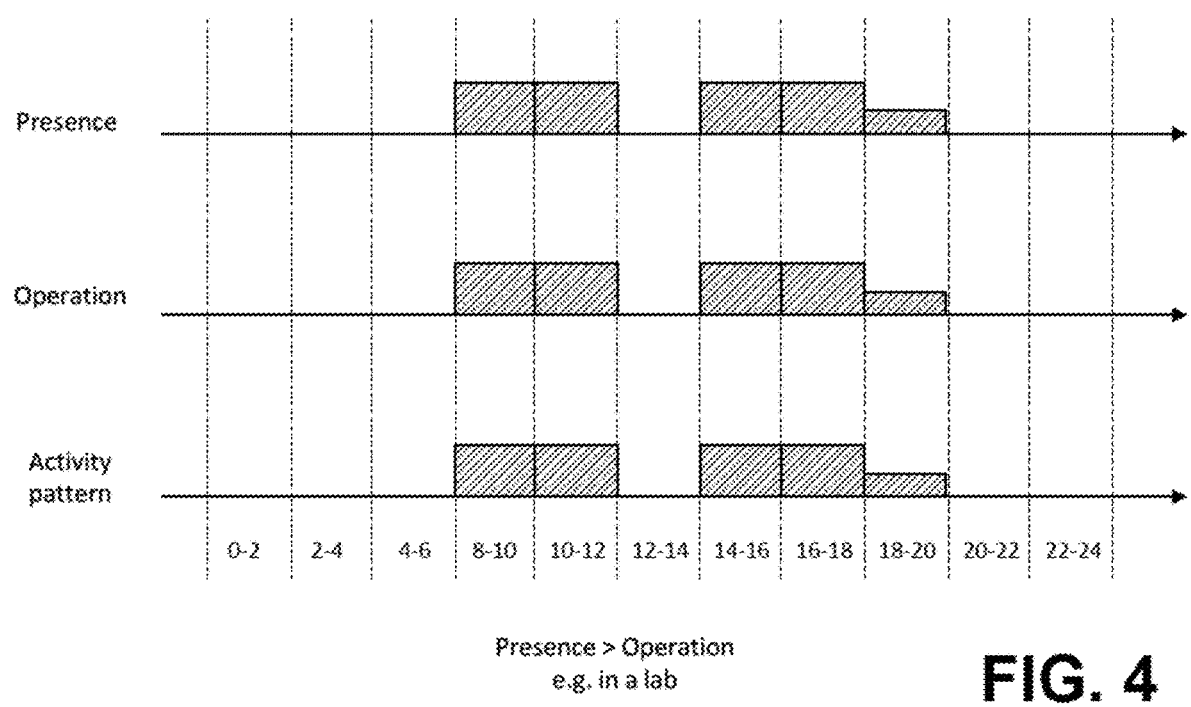
FIG. 4 illustrates a timeline illustrating detection of activity and activity pattern specific to a use case in a laboratory setting, wherein presence in the proximity of an instrument is an indication of a need to use the instrument according to an embodiment of the present disclosure.

FIG. 4 illustrates a timeline of detection of activity and activity pattern specific to a use case in a laboratory setting, wherein presence in the proximity of an instrument can be an indication of a need to use the instrument.

Figure 5:
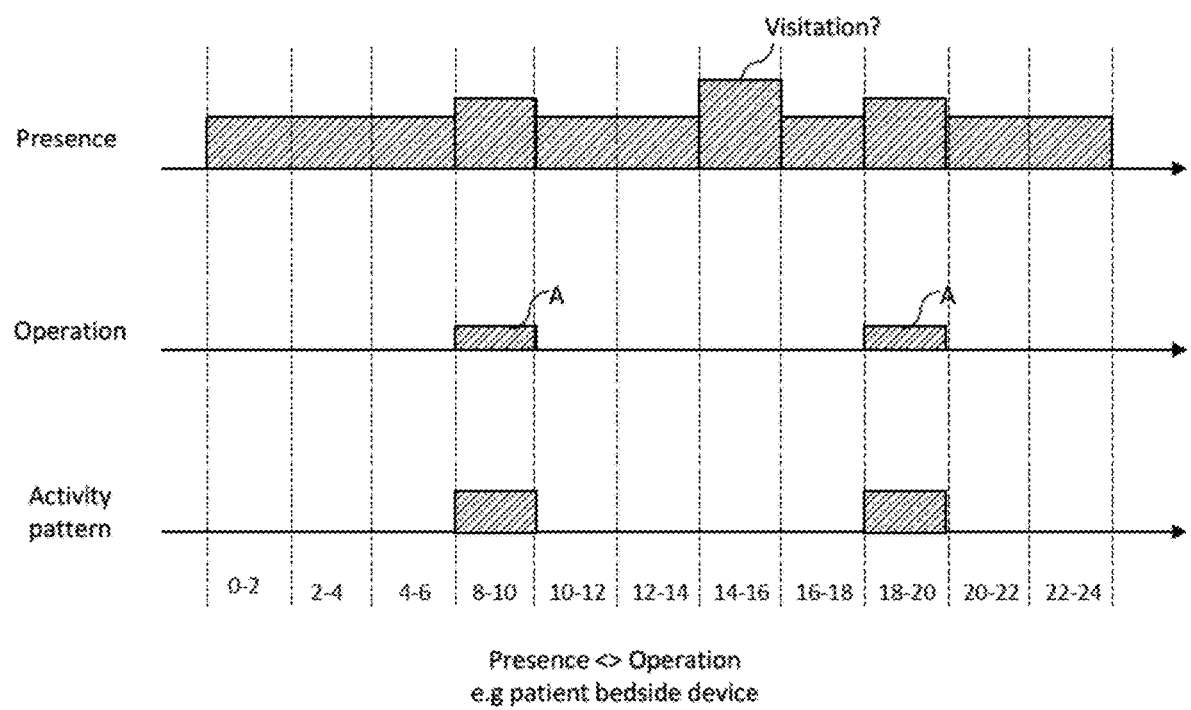
FIG. 5 illustrates a timeline illustrating detection of activity and activity pattern specific to a use case in a patient bedside setting, wherein presence in the proximity of an instrument is not necessarily an indication of a need to use the instrument according to an embodiment of the present disclosure.

FIG. 5 shows a timeline of detection of activity and activity pattern specific to a use case in a patient bedside setting, wherein presence in the proximity of an instrument may not necessarily be an indication of a need to use the instrument since the patient is present continuously. In such a use case, the processor can take into consideration only activity of the second type in scheduling maintenance processes.

Figure 6:
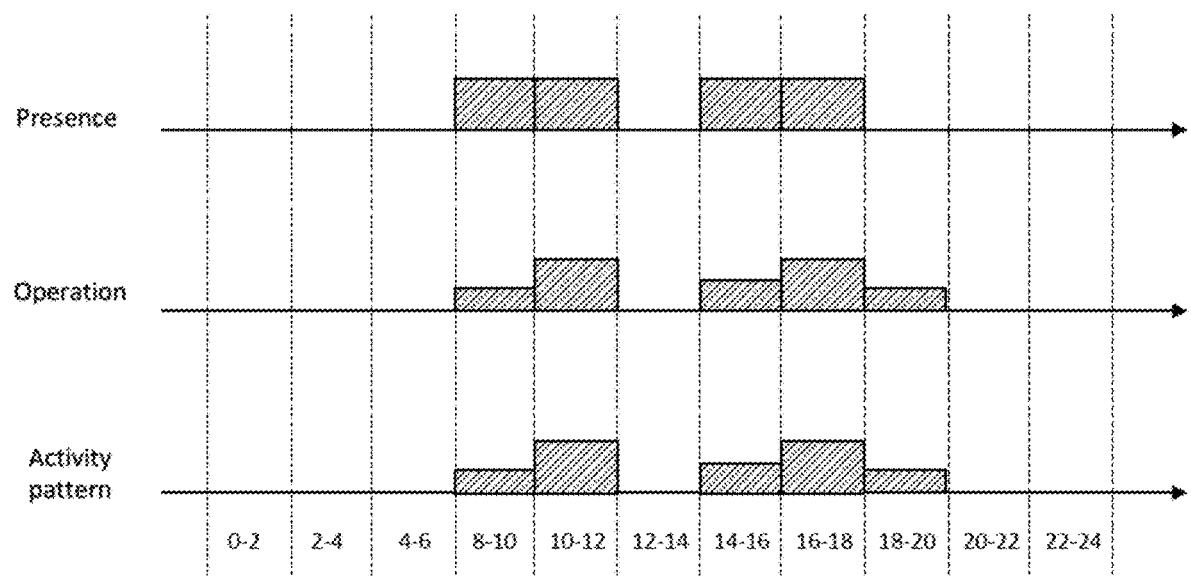
FIG. 6 illustrates a timeline illustrating detection of activity and activity pattern specific to a use case in a physician's office setting, wherein instruments are sometimes in use beyond presence, e.g. to complete started tests, according to an embodiment of the present disclosure.
Figure 7:
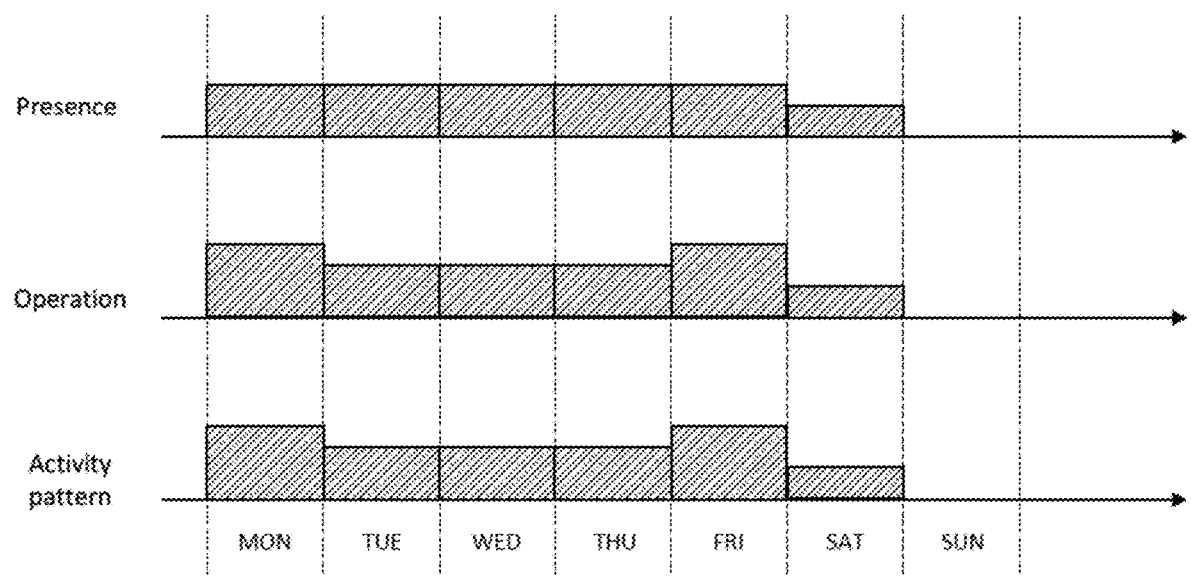
FIG. 7 illustrates a timeline illustrating detection of activity and activity pattern, based on days of a week, illustrating lower use on Saturdays and no use on Sundays according to an embodiment of the present disclosure.

FIG. 6, on the other hand, illustrates detection of activity and activity pattern specific to a use case in a physician's office setting; wherein instruments can sometimes be in use beyond presence, for example, to complete started tests FIG. 7 illustrates a different granularity of the activity pattern, based on days of a week, illustrating lower use on Saturdays and no use on Sundays.

According to further embodiments, the processor can be configured to determine detectable characteristics repeatedly associated with the second group of activity (presence but no usage of instruments). For example, the processor can determine that persons wearing a particular color and/or type of clothing/uniform are present around the instruments but never using it (e.g., cleaning staff). On the other hand, the processor can determine that persons wearing a different color and/or type of clothing/uniform always use the instruments when they are present around the instruments (e.g., lab technicians, nurses).

The processor can then calculate the probability of use of the diagnostic instrument by disregarding subsequent detections of activity of the second group having such characteristics repeatedly associated with the second group of activity. This can ensure that laboratory instruments can perform maintenance activities at times/time intervals when there is activity around the instruments but that activity does (with a high probability) not require use of the instruments.

Also, facial characteristics (e.g., face ID) of persons associated with the detected activity may also be used, for example, in connection with a database comprising the facial characteristics of personnel who are active users of the laboratory instruments.

Machine learning techniques may also be employed in order to constantly improve the determination of the right characteristics respectively with the correct probability of use of the instruments based on the processing of signals of the detection unit.

Figure 8:
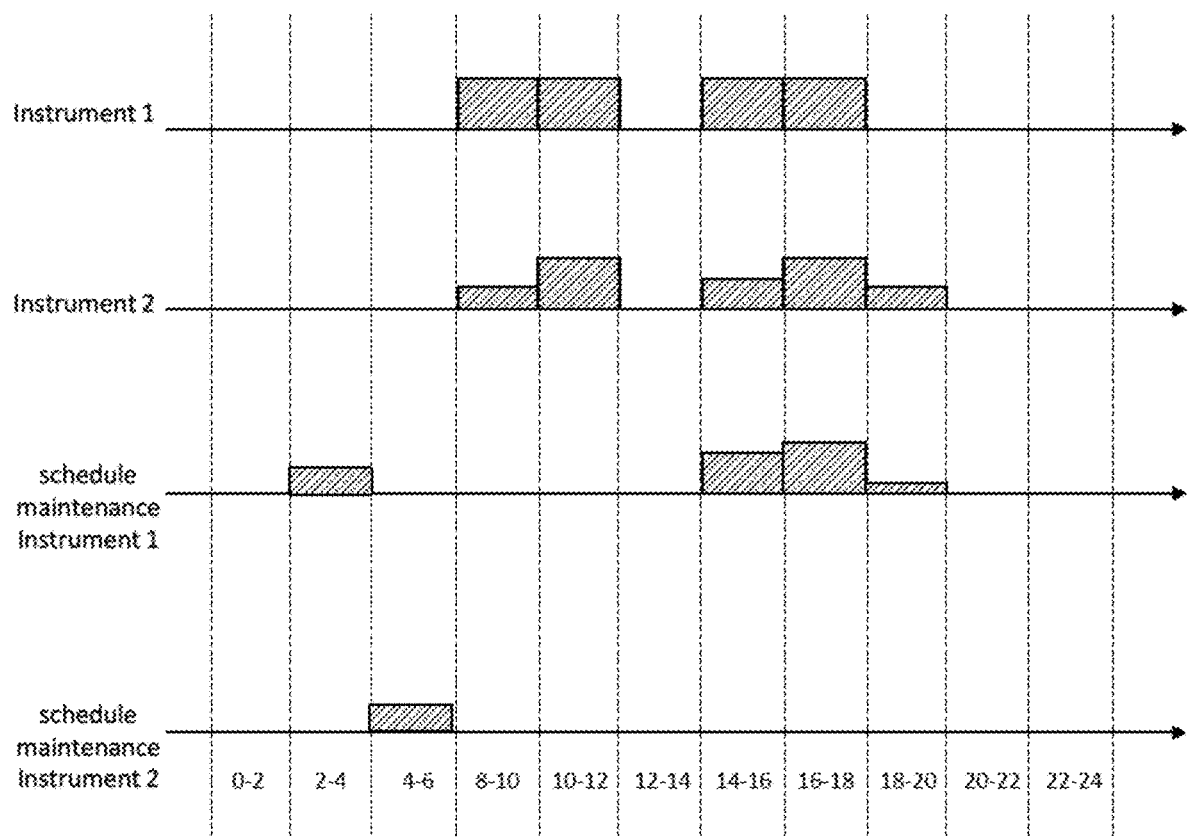
FIG. 8 illustrates a timeline illustrating detection of activity and activity pattern over a plurality of diagnostic instruments and staggered scheduling of maintenance according to an embodiment of the present disclosure.

Turing now to FIG. 8, detection of activity and activity pattern over a plurality of diagnostic instruments and staggered scheduling of maintenance shall be described. In order to optimize healthcare environments having a plurality of instruments, activity in the proximity of a plurality of diagnostic instruments can be detected and a central control unit can be employed to determine an activity pattern by processing activity detected with respect to the plurality of diagnostic instruments. To prevent situations where no diagnostic instrument is available for patient testing, the central control unit can schedule maintenance processes of the plurality of diagnostic instruments such as to avoid all instruments executing a maintenance process at the same time.

In order to avoid a false activity pattern being applied, according to further embodiments, the instruments can be configured such that the activity pattern can be reset when the instrument is relocated.

Figure 9:
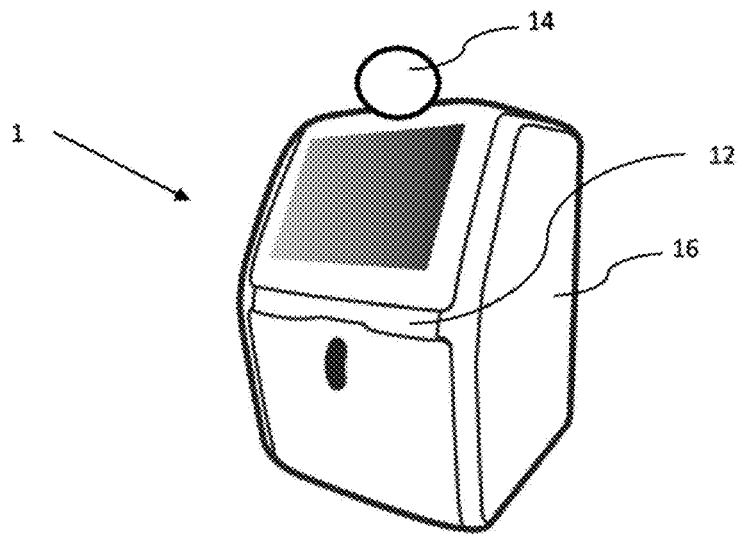
FIG. 9 illustrates highly schematic diagram of the disclosed diagnostic instrument according to an embodiment of the present disclosure.

FIG. 9 shows a highly schematic diagram of an embodiment of the disclosed diagnostic instrument 1 for analyzing a biological sample. The diagnostic instrument 1 can comprise an analytical unit 12 configured to carry out one or more analytical processing steps on the biological sample to determine presence, absence and/or concentration of one or more analyte(s) in the biological sample. Furthermore, the diagnostic instrument 1 can comprises or can be connected to a detection unit 14 configured to detect presence, movement and/or activity in the proximity of the diagnostic instrument 1. The diagnostic instrument 1 can also comprise or can be connected to a control unit 16 configured to carry out the method herein disclosed.

According to some embodiments, the detection unit 14 can comprises one or more of a motion sensor, a proximity sensor (such as RADAR or LIDAR), an image/video capturing device plus image analysis, a light intensity sensor, a microphone, and/or a connection to the user interface of the instrument.

Figure 10:
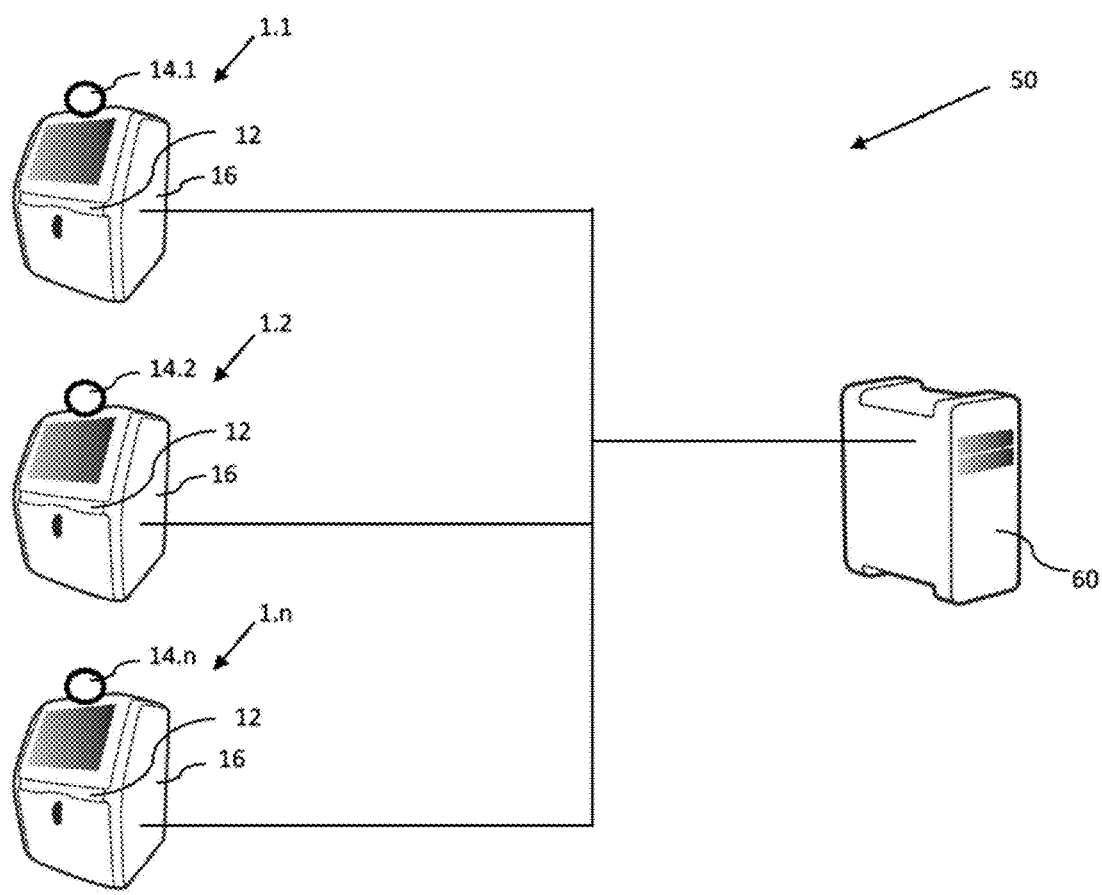
FIG. 10 illustrates highly schematic block diagram of the disclosed analytical system according to an embodiment of the present disclosure.

FIG. 10 shows an analytical system 50 comprising a plurality of diagnostic instruments 1.1-1.n for analyzing biological samples, each diagnostic instruments 1.1-1.n comprising an analytical unit 12 configured to carry out one or more analytical processing steps on the biological sample to determine presence, absence and/or concentration of one or more analyte(s) in the biological sample. The analytical system 50 can further comprise one or more detection unit(s) 14 configured to detect presence, movement and/or activity of an operator in the proximity of the plurality of diagnostic instruments 1.1-1.n. A central control unit 60 can be communicatively connected to the plurality of diagnostic instruments 1.1-1.n and the one or more detection unit(s) 14, the control unit 60 being configured to carry out the method disclosed herein.

The present disclosure can further relate to a computer program product comprising instructions which, when executed by a processor of a diagnostic instrument, causes the diagnostic instrument to perform the steps of the herein disclosed method.

The present disclosure can further relate to a computer program product comprising instructions which, when executed by a central control unit of an analytical system comprising a plurality of diagnostic instruments for analyzing biological samples, can cause the analytical system to perform the steps according to the herein disclosed method.

As used herein, a computer program product can refer to the program as a tradable product. The product may generally exist in any format, such as in a downloadable file, on a computer-readable data carrier on premise or located at a remote location (cloud). Specifically, the computer program product may be distributed over a data network (such as a cloud environment). Furthermore, not only the computer program product, but also the execution hardware may be located on premise or in a cloud environment.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method of operating a diagnostic instrument for analyzing a biological sample comprising an analytical unit configured to carry out one or more analytical processing steps on the biological sample to determine presence, absence and/or concentration of one or more analyte(s) in the biological sample, the method comprising:
   detecting activity in the proximity of the diagnostic instrument by a detection unit, wherein activity comprises at least one of a presence and/or movement of an operator in the proximity of the diagnostic instrument and/or operation of the diagnostic instrument by an operator;
   processing signals of the detection unit by a processor to determine a probability of use of the diagnostic instrument, the probability of use being directly proportional to the activity in the proximity of the diagnostic instrument; and
   carrying out maintenance processes by the diagnostic instrument such as not to conflict with the activity, wherein a maintenance process conflicts with the activity in response to determining that a probability of use of the diagnostic instrument is above a usage probability threshold.

2. The method according to claim 1, further comprising, at least one of interrupting and/or postponing maintenance processes by the diagnostic instrument in response to determining that the probability of use of the diagnostic instrument is above a usage probability threshold.

3. The method according to claim 1, further comprising, determining by the processor an activity pattern based on signals of the detection unit, the activity pattern being indicative of a probability of use at a specific time(s) and/or in a specific time interval;
   scheduling maintenance processes of a second type with an expected duration longer than a threshold duration by the diagnostic instrument such that the probability of use of the diagnostic instrument at the time the maintenance process is scheduled to be carried out is below a usage probability threshold; and
   executing the maintenance processes as scheduled by the diagnostic instrument.

4. The method according to claim 3, further comprising, classifying activity by the processor around the instrument into:
   a first group of activity in response to determining that the detected activity comprises operation of the diagnostic instrument; and
   a second group of activity in response to determining that the detected activity comprises presence and/or movement in the proximity of the diagnostic instrument but not operation of the diagnostic instrument, wherein the probability of use of the diagnostic instrument corresponding to activity of the first group is set higher than the probability of use of the diagnostic instrument corresponding to activity of the second group.

5. The method according to claim 4, further comprising determining detectable characteristics repeatedly associated with the second group of activity by the processor; and
   setting the probability of use of the diagnostic instrument disregarding subsequent detections of activity of the second group having such characteristics repeatedly associated with the second group of activity.

6. The method according to claim 5, wherein such characteristics comprise a particular color and/or type of clothing/uniform of a person associated with the detected activity and/or facial characteristics of a person associated with the detected activity.

7. The method according to claim 4, further comprising, scheduling maintenance processes requiring operator interaction at a specific time(s) and/or in a specific time interval with a probability of the second group of activity above an operator presence probability threshold.

8. The method according to claim 3, wherein determining an activity pattern comprises one or more of the following: detecting activity using the detection unit at predetermined time intervals, calculating the probability of use in a specific time interval as an average or mean percentage of detected activity in each time interval, and/or identifying time intervals in response to determining that a probability of use in the proximity of the diagnostic instrument is above an intensive use threshold and pre-schedule maintenance processes of the diagnostic instrument at a time preceding time intervals above the intensive use threshold.

9. The method according to claim 3, wherein the probability of use of the activity pattern is increased for specific time(s) and/or time interval(s) in which instrument operation was detected immediately after completion of a maintenance process of the diagnostic instrument.

10. The method according to claim 3, wherein determining an activity pattern comprises one or more of the following: retrieving (from a database) an operator work schedule, determining a correlation between the operator work schedule and detected activity, and/or extrapolate activity to entire work schedule based on said correlations.

11. The method according to claim 3, further comprising, distinguishing between maintenance processes of a first type of maintenance processes having a first expected duration and a second type of maintenance processes having a second expected duration, the second duration being longer than the first duration;
scheduling a maintenance process of a first type by the diagnostic instrument such that the probability of use of the diagnostic instrument, at the time the maintenance process of the first type is scheduled to be carried out, is below a first usage probability threshold; and
scheduling a maintenance process of a second by the diagnostic instrument such that the probability of use of the diagnostic instrument, at the time the maintenance process of the second type is scheduled to be carried out, is below a second usage probability threshold, the second usage probability threshold being lower than the first usage probability threshold.

12. The method according to claim 3, further comprising,
detecting activity in the proximity of a plurality diagnostic instruments;
determining an activity pattern by processing activity detected with respect to the plurality of diagnostic instruments by a central control unit; and
scheduling maintenance processes of the plurality of diagnostic instruments by the central control unit such as to avoid that all diagnostic instruments are executing a maintenance process at the same time.

13. A diagnostic instrument for analyzing a biological sample, the diagnostic instrument comprising:
an analytical unit configured to carry out one or more analytical processing steps on the biological sample to determine presence, absence and/or concentration of one or more analyte(s) in the biological sample;
a detection unit configured to detect presence, movement and/or activity in the proximity of the diagnostic instrument; and
a control unit configured to carry out the method of claim 1.

14. The diagnostic instrument according to claim 13, wherein the detection unit comprises one or more of: a motion sensor, a proximity sensor, an image/video capturing device plus image analysis, a light intensity sensor, a microphone, and/or a connection to the user interface of the diagnostic instrument.

15. A non-transitory computer readable medium comprising instructions which, when executed by a processor of a diagnostic instrument causes the diagnostic instrument to perform the steps of the method according to claim 1.

* * * * *